United States Patent [19]

Hayakawa et al.

[11] Patent Number: 4,985,345

[45] Date of Patent: Jan. 15, 1991

[54] RECORDING MATERIAL

[75] Inventors: Kunio Hayakawa, Gotenba; Hiromi Furuya, Shimizu; Hisanori Shimada, Numazu; Masahiro Nakata, Kawanishi; Kaoru Kodera, Toyonaka; Kouji Oohara, Osaka; Nobuo Akagi, Sakai, all of Japan

[73] Assignee: Ricoh Company, Ltd., Tokyo, Japan

[21] Appl. No.: 468,285

[22] Filed: Jan. 22, 1990

[30] Foreign Application Priority Data

Feb. 2, 1989 [JP] Japan .................................. 1-22483
Jun. 29, 1989 [JP] Japan ................................. 1-169148

[51] Int. Cl.$^5$ ............................ G03C 1/73; B41M 5/20
[52] U.S. Cl. ................................... 430/335; 430/338; 430/945; 503/220
[58] Field of Search ................ 430/335, 338, 945; 503/220

[56] References Cited

U.S. PATENT DOCUMENTS 4,119,776 10/1978 Fourber ........................ 503/220

Primary Examiner—Paul R. Michl
Assistant Examiner—Ashley I. Pezzner
Attorney, Agent, or Firm—Oblon, Spivak, McClelland, Maier & Neustadt

[57] ABSTRACT

A recording material employing at least one leuco dye having formula (I), which is colored when brought into contact with a color developer capable of inducing color formation in the leuco dye:

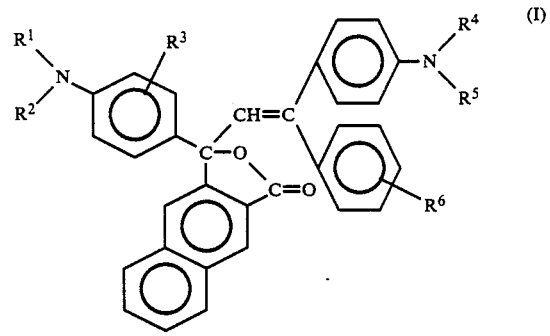

wherein $R^1$ and $R^2$ each represent an alkyl group having 1 to 6 carbon atoms, a cycloalkyl group, an unsubstituted or substituted aralkyl group, or an unsubstituted or substituted aryl group, which $R^1$ and $R^2$ may form a ring in combination or a morpholine ring through an oxygen atom; $R^3$ represents hydrogen, an alkyl group having 1 to 4 carbon atoms, an alkoxyl group having 1 to 4 carbon atoms or an aralkyloxy group; $R^4$ and $R^5$ each represent an alkyl group having 1 to 4 carbon atoms; and $R^6$ represents hydrogen, an alkyl group having 1 to 4 carbon atoms or a halogen.

22 Claims, No Drawings

RECORDING MATERIAL

BACKGROUND OF THE INVENTION

1. Field of the Invention

The present invention relates to a recording material which is capable of yielding images having a high absorption intensity in a near infrared region, especially used as a thermosensitive recording sheet and a pressure-sensitive recording sheet.

2. Discussion of Background

Recording materials using leuco dyes are conventionally known, as shown in Japanese patent Publication No. 45-14039. These recording materials, which are utilized as pressure-sensitive recording sheets and thermosensitive recording sheets, are increasingly used year by year.

Leuco dyes in general use are triphenylmethane-type leuco dyes, fluoran-type leuco dyes, phenothiazine-type leuco dyes and auramine-type leuco dyes. These leuco dyes produce their own particular color tones and are selectively used depending on the application.

However, the above dyes have been developed, with an emphasis on the improvement of the color tone, that is, on the improvement of the absorption in the visible light region. In fact, dyes which can absorb near infrared rays having a wavelength of 700 to 1,000 nm have scarcely been developed.

As a semiconductor laser has become prevalent, a tendency to read recorded images such as bar codes by use of the semiconductor laser is growing. A demand for a thermosensitive recording sheet and a pressure-sensitive recording sheet which can exhibit a sufficient absorption intensity in a near infrared region for reading is also increasing. In particular, the spotlight of attention is focussed upon the wavelength range of the semiconductor laser beam from 650 to 800 nm. Accordingly, a demand for a pressure-sensitive recording sheet and a thermosensitive recording sheet capable of yielding images having a sufficient absorption intensity for reading within the above wavelength range is especially increasing.

A variety of the leuco dyes capable of absorbing light in a near infrared region and various thermosensitive recording materials and pressure-sensitive recording materials using the above leuco dyes are conventionally proposed. For example, phthalide compounds containing two vinyl groups are disclosed in Japanese Laid-Open patent application Nos. 51-121035, 58-157779, 60-27589 and 62-243653; and sulfonylmethane compounds are disclosed in Japanese Laid-Open patent application No. 60-231766. Furthermore, as the leuco dyes having a sufficient absorption intensity in the near infrared region of 650 to 800 nm, phthalide compounds having one vinyl group are disclosed in Japanese Laid-Open patent application Nos. 51-121037, 57-167979 and 63-165379.

However, the above-mentioned leuco dyes capable of absorbing near infrared rays and the recording materials using the same have their own shortcomings. For example, although the phthalide compounds containing two vinyl groups and sulfonylmethane compounds have an absorption intensity in the near infrared region up to about 1,000 nm, their absorption intensity in an infrared region from 700 to 800 nm is not sufficient, and the backgroud of the recording materials using such leuco dyes is yellowish in color.

The phthalide compounds containing one vinyl group, which have a sufficient absorption intensity in a near infrared region up to around 800 nm, have the shortcomings in that the image formation stability is poor, and the background is easily colored and turns yellow when exposed to the sunray and fluorescent lighting over a long period of time. In addition, most of the above phthalide compounds produce a blue to green color, so that a large quantities of a fluoran-type leuco dye which produces a black color must be added to the phthalide compounds for practical use to realize the image formation in black.

SUMMARY OF THE INVENTION

Accordingly, an object of this invention is to provide a recording material capable of yielding images which sufficiently absorb light in a near infrared region of 650 to 900 nm, and produce a color inclining toward black in the visible spectrum.

Another object of the present invention is to provide a recording material with a minimized yellow discoloration of the background caused when exposed to light.

These objects of the present invention can be achieved by a recording material employing at least one leuco dye having the following formula (I), which is colored when brought into contact with a color developer capable of inducing color formation in the leuco dye:

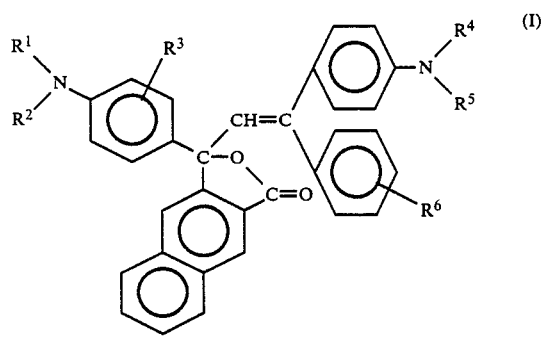

wherein $R^1$ and $R^2$ each represent an alkyl group having 1 to 6 carbon atoms, a cycloalkyl group, an aralkyl group which may have a substituent, or an aryl group which may have a substituent, which $R^1$ and $R^2$ in combination may form a ring or a morpholine ring through an oxygen atom; $R^3$ represents hydrogen, an alkyl group having 1 to 4 carbon atoms, an alkoxyl group having 1 to 4 carbon atoms or an aralkyloxy group; $R^4$ and $R^5$ each represent an alkyl group having 1 to 4 carbon atoms; and $R^6$ represents hydrogen, an alkyl group having 1 to 4 carbon atoms or a halogen.

DESCRIPTION OF THE PREFERRED EMBODIMENTS

According to the present invention, a recording material employing at least one leuco dye of the above formula (I) is provided.

In formula (I), examples of $R^1$ and $R^2$ include an alkyl group having 1 to 6 carbon atoms, such as a methyl group, an ethyl group, a propyl group, an isopropyl group, a butyl group and an isobutyl group; a cycloalkyl group such as a cyclohexyl group; an unsubstituted aryl group such as a phenyl group; an aryl group having a substituent, for example, an alkyl group having 1 to 4 carbon atoms such as a methyl group and an ethyl group, and a dialkylamino group such as a dimethylamino group and a diethylamino group; an unsubstituted aralkyl group such as a benzyl group and a phenethyl group; an aralkyl group having a substituent, for example, an alkyl group having 1 to 4 carbon atoms such as a methyl group and an ethyl group; and $R^1$ and $R^2$ in combination may represent a heterocyclic group such as a piperidino group, a pyrrolidino group and a monopholino group.

Examples of $R^3$ in formula (I) include hydrogen, an alkyl group having 1 to 4 carbon atoms, such as a methyl group, an ethyl group, a propyl group, an isopropyl group, a butyl group and an isobutyl group; an alkoxyl group having 1 to 4 carbon atoms, such as a methoxy group, an ethoxy group, a propoxy group and an isopropoxy group; and an aralkyloxy group such as a benzyloxy group and a phenylethyloxy group.

Examples of $R^4$ and $R^5$ in formula (I) include an alkyl group having 1 to 4 carbon atoms, such as a methyl group, an ethyl group, a propyl group, an isopropyl group, a butyl group and an isobutyl group.

Examples of $R^6$ in formula (I) include hydrogen; an alkyl group having 1 to 4 carbon atoms, such as a methyl group, an ethyl group, a propyl group and an isopropyl group; and a halogen such as chloride and bromide.

The leuco dyes having the above formula (I) for use in the present invention, which are novel materials available in the form of a white or light-yellow crystal, can be synthesized in the following reaction scheme:

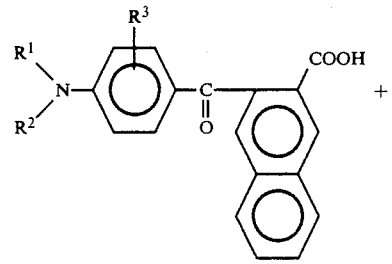

(II)

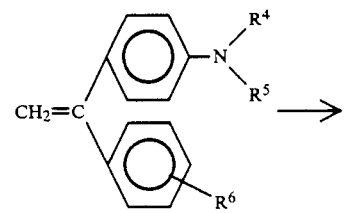

(III)

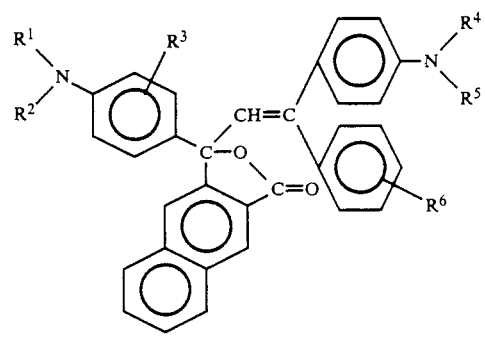

(I)

wherein $R^1$, $R^2$, $R^3$, $R^4$, $R^5$ and $R^6$ are the same as those defined in the above formula (I).

More specifically, a ketone derivative represented by the above formul (II) and an ethylene derivative of formula (III) undergo dehydration condensation in the presence of a dehydration condensing agent, whereby the leuco dye of formula (I) can be easily obtained. In the dehydration condensation, a condensing agent such as acetic anhydride, propionic anhydride, phosphorus oxychloride, sulfuric acid, polyphosphoric acid, and a variety of Friedel-Crafts catalysts can be used.

Specific examples of the leuco dyes of formula (I) for use in the present invention are shown in Table 1, but not limited to the followings:

TABLE 1

| Leuco Dye No. | $R^1$ | $R^2$ | $R^3$ (at 2-position) | $R^4$ | $R^5$ | $R^6$ (at p-position) |
|---|---|---|---|---|---|---|
| 1 | —$C_2H_5$ | —$C_2H_5$ | —$OCH_3$ | —$CH_3$ | —$CH_3$ | —Cl |
| 2 | —$C_2H_5$ | —$C_2H_5$ | —$OCH_3$ | —$CH_3$ | —$CH_3$ | —H |
| 3 | —$C_2H_5$ | —$C_2H_5$ | —$OCH_3$ | —$C_2H_5$ | —$C_2H_5$ | —H |
| 4 | —$C_2H_5$ | —$C_2H_5$ | —$OCH_2$—C₆H₅ | —$CH_3$ | —$CH_3$ | —Cl |
| 5 | —$CH_3$ | —$CH_3$ | —$OCH_3$ | —$CH_3$ | —$CH_3$ | —Cl |
| 6 | —$CH_3$ | —$CH_3$ | —$OCH_3$ | —$CH_3$ | —$CH_3$ | —H |
| 7 | —$CH_3$ | —$CH_3$ | —$CH_3$ | —$CH_3$ | —$CH_3$ | —H |
| 8 | —$CH_3$ | —$CH_3$ | —$CH_3$ | —$CH_3$ | —$CH_3$ | —Cl |
| 9 | —$C_4H_9$ | —$C_4H_9$ | —$OCH_3$ | —$CH_3$ | —$CH_3$ | —H |
| 10 | —$C_4H_9$ | —$C_4H_9$ | —$OCH_3$ | —$CH_3$ | —$CH_3$ | —Cl |
| 11 | —$C_4H_9$ | —$C_4H_9$ | —$OCH_2$—C₆H₅ | —$CH_3$ | —$CH_3$ | —Cl |

TABLE 1-continued

| Leuco Dye No. | R¹ | R² | R³ (at 2-position) | R⁴ | R⁵ | R⁶ (at p-position) |
|---|---|---|---|---|---|---|
| 12 | —C₄H₉ | —C₄H₉ | 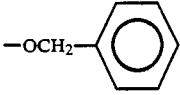—OCH₂—C₆H₅ | —CH₃ | —CH₃ | —H |
| 13 | —C₂H₅ | 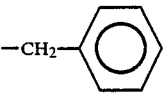—CH₂—C₆H₅ | —H | —CH₃ | —CH₃ | —Cl |
| 14 | —C₂H₅ | 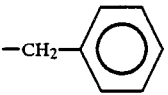—CH₂—C₆H₅ | —H | —CH₃ | —CH₃ | —H |
| 15 | —C₂H₅ | —C₂H₅ | —H | —CH₃ | —CH₃ | —Cl |
| 16 | —C₂H₅ | —C₂H₅ | —H | —CH₃ | —CH₃ | —H |
| 17 | —CH₃ | —CH₃ | —H | —CH₃ | —CH₃ | —H |
| 18 | —CH₃ | —CH₃ | —H | —CH₃ | —CH₃ | —Cl |
| 19 |  |  | —H | —CH₃ | —CH₃ | —H |
| 20 |  |  | —H | —CH₃ | —CH₃ | —Cl |
| 21 | —C₆H₄—CH₃ | 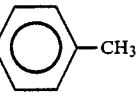—C₆H₄—CH₃ | —H | —CH₃ | —CH₃ | —H |
| 22 | 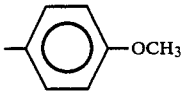—C₆H₄—OCH₃ | —CH₃ | —H | —CH₃ | —CH₃ | —H |
| 23 | 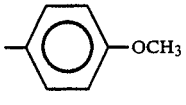—C₆H₄—OCH₃ | —CH₃ | —H | —CH₃ | —CH₃ | —Cl |
| 24 | 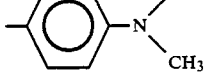—C₆H₄—N(CH₃)₂ | —CH₃ | —H | —CH₃ | —CH₃ | —Cl |
| 25 | 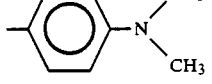—C₆H₄—N(CH₃)₂ | —CH₃ | —H | —CH₃ | —CH₃ | —H |
| 26 | —C₂H₅ | —C₂H₅ | —OCH₃ | —CH₃ | —CH₃ | —Br |
| 27 | —C₄H₉ | —C₄H₉ | —OCH₃ | —CH₃ | —CH₃ | —Br |
| 28 | —C₂H₅ | 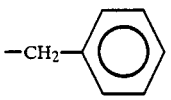—CH₂—C₆H₅ | —H | —CH₃ | —CH₃ | —Br |
| 29 |  |  | —H | —CH₃ | —CH₃ | —Br |

TABLE 1-continued
| Leuco Dye No. | R¹ | R² | R³ (at 2-position) | R⁴ | R⁵ | R⁶ (at p-position) |
|---|---|---|---|---|---|---|
| 30 |  | | —H | —CH₃ | —CH₃ | —H |
| 31 |  | | —H | —CH₃ | —CH₃ | —Cl |
| 32 |  | | —H | —CH₃ | —CH₃ | —Cl |
| 33 |  | | —H | —CH₃ | —CH₃ | —H |
| 34 | 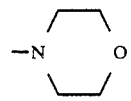 | | —H | —CH₃ | —CH₃ | —H |
| 35 | 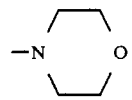 | | —H | —CH₃ | —CH₃ | —Cl |
| 36 | 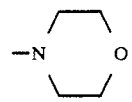 | | —H | —CH₃ | —CH₃ | —Br |
| 37 | 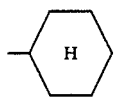 | —CH₃ | —H | —CH₃ | —CH₃ | —H |
| 38 | 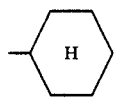 | —CH₃ | —H | —CH₃ | —CH₃ | —Cl |
| 39 | 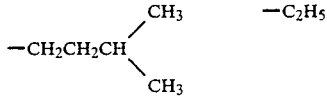 | —C₂H₅ | —H | —CH₃ | —CH₃ | —Cl |
| 40 | 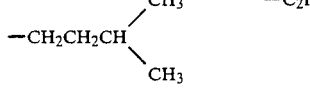 | —C₂H₅ | —H | —CH₃ | —CH₃ | —H |
| 41 | 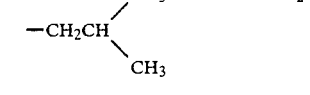 | —C₂H₅ | —H | —CH₃ | —CH₃ | —Cl |
| 42 | 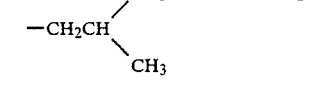 | —C₂H₅ | —H | —CH₃ | —CH₃ | —H |
| 43 | —CH₃ | —C₄H₉ | —H | —CH₃ | —CH₃ | —H |
| 44 | —CH₃ | —C₄H₉ | —H | —CH₃ | —CH₃ | —Cl |

TABLE 1-continued

| Leuco Dye No. | R¹ | R² | R³ (at 2-position) | R⁴ | R⁵ | R⁶ (at p-position) |
|---|---|---|---|---|---|---|
| 45 | —C₂H₅ | —C₂H₅ | —OCH₃ | —CH₃ | —CH₃ | —CH₃ |
| 46 | —C₂H₅ | —C₂H₅ | —OCH₂—C₆H₅ | —CH₃ | —CH₃ | —CH₃ |
| 47 | —CH₃ | —CH₃ | —OCH₃ | —CH₃ | —CH₃ | —CH₃ |
| 48 | —C₄H₉ | —C₄H₉ | —OCH₃ | —CH₃ | —CH₃ | —CH₃ |
| 49 | —C₄H₉ | —C₄H₉ | —OCH₂—C₆H₅ | —CH₃ | —CH₃ | —CH₃ |
| 50 | —C₂H₅ | —CH₂—C₆H₅ | —H | —CH₃ | —CH₃ | —CH₃ |
| 51 | —CH₃ | —CH₃ | —H | —CH₃ | —CH₃ | —CH₃ |
| 52 | —C₆H₅ | —C₆H₅ | —H | —CH₃ | —CH₃ | —CH₃ |
| 53 | \pyrrolidino (—N< ring)\ | | —H | —CH₃ | —CH₃ | —CH₃ |
| 54 | \piperidino (—N< ring)\ | | —H | —CH₃ | —CH₃ | —CH₃ |
| 55 | \morpholino (—N< ring with O)\ | | —H | —CH₃ | —CH₃ | —CH₃ |
| 56 | —C₆H₁₁ (cyclohexyl) | —CH₃ | —OCH₃ | —CH₃ | —CH₃ | —H |
| 57 | —C₂H₄CH(CH₃)CH₃ | —C₂H₅ | —OCH₃ | —CH₃ | —CH₃ | —H |
| 58 | —CH₂CH(CH₃)CH₃ | —C₂H₅ | —OCH₃ | —CH₃ | —CH₃ | —H |
| 59 | —CH₂CH(CH₃)CH₃ | —C₂H₅ | —OCH₃ | —CH₃ | —CH₃ | —Cl |
| 60 | —C₂H₅ | —C₂H₅ | —H | —CH₃ | —CH₃ | —CH₃ |
| 61 | —C₄H₉ | —C₄H₉ | —H | —CH₃ | —CH₃ | —H |
| 62 | —C₄H₉ | —C₄H₉ | —H | —CH₃ | —CH₃ | —Cl |
| 63 | —C₄H₉ | —C₄H₉ | —H | —CH₃ | —CH₃ | —CH₃ |

TABLE 1-continued

| Leuco Dye No. | R¹ | R² | R³ (at 2-position) | R⁴ | R⁵ | R⁶ (at p-position) |
|---|---|---|---|---|---|---|
| 64 | —C$_2$H$_5$ | —C$_2$H$_5$ | —OCH$_2$—C$_6$H$_5$ | —CH$_3$ | —CH$_3$ | —H |
| 65 | —CH$_3$ | —CH$_3$ | —OCH$_2$—C$_6$H$_5$ | —CH$_3$ | —CH$_3$ | —H |
| 66 | —CH$_3$ | —CH$_3$ | —OCH$_2$—C$_6$H$_5$ | —CH$_3$ | —CH$_3$ | —Cl |
| 67 | —CH$_3$ | —CH$_3$ | —OCH$_2$—C$_6$H$_5$ | —CH$_3$ | —CH$_3$ | —CH$_3$ |
| 68 | —CH$_3$ | —CH$_3$ | —CH$_3$ | —CH$_3$ | —CH$_3$ | —CH$_3$ |
| 69 | —C$_6$H$_{11}$ (cyclohexyl) | —CH$_3$ | —OCH$_3$ | —CH$_3$ | —CH$_3$ | —Cl |
| 70 | —C$_6$H$_{11}$ (cyclohexyl) | —CH$_3$ | —OCH$_3$ | —CH$_3$ | —CH$_3$ | —CH$_3$ |
| 71 | —C$_2$H$_4$CH(CH$_3$)$_2$ | —C$_2$H$_5$ | —OCH$_3$ | —CH$_3$ | —CH$_3$ | —Cl |
| 72 | —C$_2$H$_4$CH(CH$_3$)$_2$ | —C$_2$H$_5$ | —OCH$_3$ | —CH$_3$ | —CH$_3$ | —CH$_3$ |
| 73 | —C$_3$H$_7$ | —CH$_3$ | —OCH$_3$ | —CH$_3$ | —CH$_3$ | —H |
| 74 | —C$_3$H$_7$ | —CH$_3$ | —OCH$_3$ | —CH$_3$ | —CH$_3$ | —CH$_3$ |

The leuco dyes represented by formula (I) for use in the present invention produce a green tinged black color to a red tinged black color. To control the color tone of the leuco dyes or to adjust the absorption characteristics thereof, the leuco dyes of formula (I) can be used together with other conventional leuco dyes. As the above-mentioned conventional leuco dyes, any leuco dyes used in the conventional recording materials can be employed. For example, triphenylmethane-type leuco compounds, fluoran-type leuco compounds, phenothiazine-type leuco compounds, auramine-type leuco compounds, and spiropyran-type leuco compounds are preferably employed. Specific examples of those leuco dyes are as follows:

3,3-bis(p-dimethylaminophenyl)-phthalide,
3,3-bis(p-dimethylaminophenyl)-6-dimethylaminophthalide (or Crystal Violet Lactone),
3,3-bis(p-dimethylaminophenyl)-6-diethylaminophthalide,
3,3-bis(p-dimethylaminophenyl)-6-chlorophthalide,
3,3-bis(p-dibutylaminophenyl)-phthalide,
3-cyclohexylamino-6-chlorofluoran,
3-dimethylamino-5,7-dimethylfluoran,
3-diethylamino-7-chlorofluoran,
3-diethylamino-7-methylfluoran,
3-diethylamino-7,8-benzfluoran,
3-diethylamino-6-methyl-7-chlorofluoran,
3-(N-p-tolyl-N-ethylamino)-6-methyl-7-anilinofluoran,
3-pyrrolidino-6-methyl-7-anilinofluoran,
2-[N-(3'-trifluoromethylphenyl)amino]-6-diethylaminofluoran,
2-[3,6-bis(diethylamino)-9-(o-chloroanilino)xanthylbenzoic acid lactam],
3-diethylamino-6-methyl-7-(m-trichloromethylanilino)-fluoran,
3-diethylamino-7-(o-chloroanilino)fluoran,
3-dibutylamino-7-(o-chloroanilino)fluoran,
3-N-methyl-N-amylamino-6-methyl-7-anilinofluoran,
3-N-methyl-N-cyclohexylamino-6-methyl-7-anilinofluoran,
3-diethylamino-6-methyl-7-anilinofluoran, 3-(N,N-diethylamino)-5-methyl-7-(N,N-dibenzylamino)fluoran,
Benzoyl leuco methylene blue,
6'-chloro-8'-methoxy-benzoindolino-spiropyran,
6'-bromo-3'-methoxy-benzoindolino-spiropyran,
3-(2'-hydroxy-4'-dimethylaminophenyl)-3-(2'-methoxy-5'-chlorophenyl)phthalide,
3-(2'-hydroxy-4'-dimethylaminophenyl)-3-(2'-methoxy-5'nitrophenyl)phthalide,
3-(2'-hydroxy-4'-diethylaminophenyl)-3-(2'-methoxy-5'-methylphenyl)phthalide,
3-(2'-methoxy-4'-dimethylaminophenyl)-3-(2'-hydroxy-4'-chloro-5'-methylphenyl) phthalide,
3-morpholino-7-(N-propyl-trifluoromethylanilino)fluoran,
3-pyrrolidino-7-trifluoromethylanilinofluoran,
3-diethylamino-5-chloro-7-(N-benzyl-trifluoromethylanilino)fluoran,
3-pyrrolidino-7-(di-p-chlorophenyl)methylaminofluoran,
3-diethylamino-5-chloro-7-(α-phenylethylamino)fluoran,
3-(N-ethyl-p-toluidino)-7-(α-phenylethylamino)fluoran,
3-diethylamino-7-(o-methoxycarbonylphenylamino)fluoran,
3-diethylamino-5-methyl-7-(α-phenylethylamino)fluoran,
3-diethylamino-7-piperidinofluoran,
2-chloro-3-(N-methyltoluidino)-7-[p-n-butylanilino)fluoran,
3-(N-benzyl-N-cyclohexylamino)-5,6-benzo-7-α-naphthyl-amino-4'-bromofluoran,
3-diethylamino-6-methyl-7-mesidino-4',5'-benzofluoran, and
3-diethylamino-6-methyl-7-(2',4'-dimethylanilino) fluoran.

As the color developers for use in combination with the above leuco dyes in the present invention, a variety of electron acceptors or oxidizing agents capable of inducing color formation in the leuco dyes can be employed.

Examples of the color developer for use in the present invention include inorganic acids, organic acids, phenolic materials and phenolic resins, for example:
bentonite,
zeolite,
acidic terra alba,
activated clay,
silica gel,
phenolic resin,
4,4'-isopropylidenebisphenol,
4,4'-isopropylidenebis(o-methylphenol),
4,4'-sec-butylidenebisphenol,
4,4'-isopropylidenebis(2-tert-butylphenol),
4,4'-cyclohexylidenediphenol,
4,4'-isopropylidenebis(2-chlorophenol),
2,2'-methylenebis(4-methyl-6-tert-butylphenol),
2,2'-methylenebis(4-ethyl-6-tert-butylphenol),
4,4'-butylidenebis(6-tert-butyl-2-methyl)phenol,
1,1,3-tris(2-methyl-4-hydroxy-5-tertbutylphenyl)butane,
1,1,3-tris(2-methyl-4-hydroxy-5cyclohexylphenyl)butane,
4,4'-thiobis(6-tert-butyl-2-methyl)phenol,
4,4'-diphenolsulfone,
4,2'-diphenolsulfone,
4-isopropoxy-4'-hydroxydiphenylsulfone,
4-benzyloxy-4'-hydroxydiphenylsulfone,
4,4'-diphenolsulfoxide,
isopropyl p-hydroxybenzoate,
benzyl p-hydroxybenzoate,
benzyl protocatechuate,
stearyl gallate,
lauryl gallate,
octyl gallate,
1,7-bis(4-hydroxyphenylthio)-3,5-dioxaheptane,
1,5-bis(4-hydroxyphenylthio)-3-oxapentane,
1,3-bis(4-hydroxyphenylthio)-propane,
2,2'-methylenebis(4-ethyl-6-tert-butylphenol),
1,3-bis(4-hydroxyphenylthio)-2-hydroxypropane,
N,N'-diphenylthiourea,
N,N'-di(m-chlorophenyl)thiourea,
salicylanilide,
5-chloro-salicylanilide,
salicyl-o-chloroanilide,
2-hydroxy-3-naphthoic acid,
antipyrine complex of zinc thiocyanate,
zinc salt of 1-acetyloxy-3-naphthoic acid,
2-hydroxy-1-naphthoic acid,
1-hydroxy-2-naphthoic acid,
zinc hydroxynaphthoic acid,
aluminum hydroxynaphthoic acid,
calcium hydroxynaphthoic acid,
bis(4-hydroxyphenyl)methyl acetate,
bis(4-hydroxyphenyl)benzyl acetate,
1,3-bis(4-hydroxy)cumylbenzene,
1,4-bis(4-hydroxy)cumylbenzene,
2,4'-diphenolsulfone,
3,3'-diallyl-4,4'-diphenolsulfone,
α,α-bis(4-hydroxyphenyl)-α-methyltoluene,
tetrabromobisphenol A,
tetrabromobisphenol S, and
3,4-dihydroxy-4'-methyldiphenylsulfone.

In order to obtain a thermosensitive recording material according to the present invention, a variety of conventional binder agents can be employed for binding the above-mentioned leuco dyes and color developers to a substrate of the thermosensitive recording material.

Furthermore, in order to obtain a pressure-sensitive recording material according to the present invention, the same binder agents can also be employed for fixing the leuco dyes in the form of microcapsules and the color developers to the substrate of the pressure-sensitive recording material.

Examples of the above binder agents for use in the present invention are polyvinyl alcohol; starch and starch derivatives; cellulose derivatives such as methoxycellulose, hydroxyethylcellulose, carboxymethylcellulose, methylcellulose and ethylcellulose; other water-soluble polymers such as sodium polyacrylate, polyvinyl pyrrolidone, acrylamide - acrylic acid ester copolymer, acrylamide - acrylic acid ester - methacrylic acid terpolymer, alkali salts of styrene - maleic anhydride copolymer, alkali salts of isobutylene - maleic anhydride copolymer, polyacrylamide, sodium alginate, gelatin and casein; emulsions of polyvinyl acetate, polyurethane, polyacrylic acid ester, polymethacrylic acid ester, vinyl chloride - vinyl acetate copolymer and ethylene - vinyl acetate copolymer; and latexes of styrene - butadiene copolymer and styrene - butadiene - acrylic acid derivative copolymer.

Further in the present invention, to obtain the thermosensitive recording materials, a variety of thermofusible materials may be used, when necessary, as a thermosensitivity increasing agent.

Specific examples of the above-mentioned thermofusible materials for use in the present invention are fatty acids such as stearic acid and behenic acid; amides of fatty acids such as stearic acid amide and palmitic acid amide; metallic salts of fatty acids such as zinc stearate, aluminum stearate, calcium stearate, zinc palmitate and zinc behenate; and p-benzylbiphenyl, terphenyl, triphenylmethane, benzyl p-benzyloxybenzoate, β-benzyloxynaphthalene, β-phenyl naphthoate, 1-hydroxy-2-phenyl naphthoate, 1-hydroxy-2-methyl naphthoate, diphenyl carbonate, dibenzyl terephthalate, dimethyl terephthalate, 1,4-dimethoxynaphthalene, 1,4-diethoxynaphthalene, 1,4-dibenzyloxy-naphthalene, 1,2-bis(phenoxy)ethane, 1,2-bis(3-methylphenoxy)ethane, 1,2-bis(4-methylphenoxy)ethane, 1,4-bis(phenoxy)butane, 1,4-bis(phenoxy)-2-butene, 1,2-bis(4-methoxyphenylthio)ethane, dibenzoylmethane, 1,4-bis (phenylthio)butane, 1,4-bis(phenylthio)-2-butene, 1,2-bis(4-methoxyphenylthio)ethane, 1,3-bis(2-vinyloxyethoxy)benzene, 1,4-bis(2-vinyloxyethoxy)benzene, p-(2-vinyloxyethoxy) biphenyl, p-aryloxybiphenyl, p-propargyloxybiphenyl, dibenzoyloxymethane, 1,3-dibenzoyloxypropane, dibenzyl disulfide, 1,1-diphenylethanol, 1,1-diphenylpropanol, p-(benzyloxy)benzyl alcohol, 1,3-diphenoxy-2-propanol, N-octadecylcarbamoyl-p-methoxycarbonylbenzene, and N-octadecylcarbamoylbenzene.

In the present invention, auxiliary additive components such as fillers, surface active agents, lubricants, and agents for preventing color formation by pressure application, which are used in the conventional thermosensitive and pressure-sensitive recording materials, can be employed when necessary.

Examples of the filler for use in the present invention are finely-divided particles of an inorganic filler such as calcium carbonate, silica, zinc oxide, titanium oxide, aluminum hydroxide, zinc hydroxide, barium sulfate, clay, talc, surface-treated calcium, and surface-treated silica, and finely-divided particles of an organic filler such as urea - formaldehyde resin, styrene - methacrylic acid copolymer, and polystyrene resin.

Examples of the lubricants for use in the present invention are higher fatty acids, and metallic salts, amides and esters thereof; and a variety of waxes such as animal wax, vegetable wax, mineral wax and petroleum wax.

A pressure-sensitive recording material according to the present invention can be prepared, for example, as follows:

Any of the above-mentioned color developers is dispersed or dissolved in water or an organic solvent by means of an appropriate dispersant. To the thus prepared dispersion, an appropriate binder agent may be added when necessary, and this dispersion is coated on a substrate such as a sheet of paper, so that a color-developer sheet is obtained. Apart from the above, a dye-forming sheet is prepared by dispersing the above leuco dye in the form of a microcapsule by means of an appropriate dispersant and coating this dispersion on a substrate such as a sheet of paper. Such a microcapsule can be prepared by the conventional methods, for instance, by the method described in U.S. Pat. No. 2,800,457.

A thermosensitive recording material using the leuco dye according to the present invention can be prepared, for example, as follows:

The above-mentioned leuco dye and the color developer, which are separately dispersed, are mixed with addition thereto of an appropriate binder agent. The thus prepared mixture is coated on a substrate such as a sheet of paper.

In this case, a coloring layer of the thermosensitive recording material may be formed by coating a coating liquid at a time. Alternatively, multi-layered type coloring layer may be formed by coating a coating liquid twice or more. Furthermore, a leuco dye dispersion and a color developer dispersion may be separately coated on the substrate.

An overcoat layer, an undercoat layer and a back layer may be provided as in the preparation of conventional thermosensitive recording materials.

According to the present invention, a thermal image transfer type recording material can be prepared by providing two substrates which support the leuco dye and the color developer, separately. Specifically, the leuco dye is dispersed or dissolved in water or a solvent. This dispersion is coated on a conventionally employed heat-resistant substrate such as a polyester film to form an image-transfer sheet, while an image-receiving sheet can be prepared by dispersing or dissolving the color developer in water or a solvent, and then coating this dispersion or solution on the other substrate.

The recording materials according to the present invention can be employed in various fields just like conventional ones. In particular, since the leuco dyes contained in the recording material according to the present invention have the advantages of a sufficient absorption intensity in a near infrared region, such recording materials can be utilized for an optical character reading apparatus, label bar-code reader and bar-code reader.

When the recording material according to the present invention is used as a thermosensitive recording adhesive label sheet, a thermosensitive coloring layer comprising the above leuco dye and the color developer is formed on the front side of the substrate, and an adhesive layer is formed on the back side of the substrate, with a disposable backing sheet attached to the adhesive layer.

Other features of this invention will become apparent in the course of the following description of exemplary embodiments, which are given for illustration of the invention and are not intended to be limiting thereof.

EXAMPLES 1 TO 20 AND COMPARATIVE EXAMPLES 1 TO 3

Liquid A and Liquid B were separately prepared by dispersing the following respective components in a ball mill:

|  | Parts by Weight |
| --- | --- |
| [Liquid A] | |
| Leuco Dye in Table 2 | 10 |
| 10% aqueous solution of polyvinyl alcohol | 10 |
| Water | 30 |
| [Liquid B] | |
| Bisphenol A | 30 |
| Stearamide | 20 |
| Calcium carbonate | 20 |
| 10% aqueous solution of polyvinyl alcohol | 70 |
| Water | 245 |

Liquid A and Liquid B were mixed with a mixing ratio by weight of 1:1, so that a thermosensitive coloring layer coating liquid was prepared. The thus prepared thermo-sensitive coloring layer coating liquid was coated on a sheet of high quality paper having a basis weight of 50 g/m², with a solid dye content of 0.5 g/m² on a dry basis, and then dried, whereby thermosensitive recording materials No. 1 to No. 20 according to the present invention and comparative thermosensitive recording materials No. 1 to No. 3 were obtained.

The thus obtained thermosensitive recording materials No. 1 to No. 20 according to the present invention and comparative thermosensitive recording materials No. 1 to No. 3 were subjected to a printing test by use of a commercially available thermal printing simulator made by Matsushita Electronic Components Co., Ltd. with an electric power of 0.45 w/dot being applied to each material over a period of 1.8 msec under the conditions that a recording time was 20 msec/line and a sub-scanning density was 3.58 lines/mm. After each thermosensitive recording material produced images, the reflectance of an image area and that of a background area were measured by a commercially available spectrophotometer (Trademark "Spectrophotometer Model-330" made by Hitachi, Ltd.) when the recording materials were exposed to rays of 680 nm and 780 nm. The PCS value of each recording material was assessed from the following formula.

$$\text{PCS Value (\%)} = \frac{\text{(Reflectance of Background)} - \text{(Reflectance of Image Area)}}{\text{Reflectance of Background}} \times 100$$

In addition, each of the aforementioned thermosensitive recording materials was subjected to a light-resistance test in such a manner that it was exposed to fluorescent lighting of 5000 lux for 100 hours. After the exposure to the fluorescent lighting, the color tone of the background was measured by a commercially available color difference meter (made by Nippon Denshoku Kogyo K.K.) and the lightness index ($L^*$), and chromaticness indices ($a^*$) and ($b^*$) in terms of $L^*a^*b^*$ color space were obtained as shown in Table 2.

The test results are given in Table 2.

| Example No. | Leuco Dye No. (in Table 1) | Color Tone | Color of Background | PCS Value (680 nm) | PCS Value (780 nm) | L* | a* | b* |
|---|---|---|---|---|---|---|---|---|
| 1 | (1) | Green Black | White | 93.7(%) | 92.9(%) | 83.1 | −3.1 | 13.0 |
| 2 | (2) | Green Black | White | 94.1 | 93.0 | 82.9 | −3.2 | 13.0 |
| 3 | (55) | Green Black | White | 94.5 | 93.1 | 83.1 | −3.2 | 13.8 |
| 4 | (8) | Green Black | White | 93.7 | 92.8 | 83.0 | −3.2 | 12.5 |
| 5 | (7) | Green Black | White | 91.3 | 91.1 | 85.3 | −2.0 | 6.5 |
| 6 | (57) | Green Black | White | 94.1 | 92.4 | 85.2 | −2.1 | 7.2 |
| 7 | (23) | Red Brown | White | 89.7 | 93.9 | 83.8 | −3.0 | 11.6 |
| 8 | (63) | Red Brown | White | 92.6 | 93.5 | 83.3 | −3.1 | 13.1 |
| 9 | (21) | Red Brown | White | 79.0 | 92.7 | 85.1 | −1.9 | 4.7 |
| 10 | (20) | Red Brown | White | 91.2 | 94.0 | 83.2 | −3.2 | 13.2 |
| 11 | (74) | Red Brown | White | 93.4 | 93.5 | 81.7 | −3.2 | 11.4 |
| 12 | (19) | Red Brown | White | 87.1 | 93.8 | 82.3 | −1.9 | 8.6 |
| 13 | (18) | Red Brown | White | 90.1 | 91.4 | 84.3 | −3.2 | 10.5 |
| 14 | (63) | Red Brown | White | 91.2 | 92.3 | 83.2 | −2.6 | 11.3 |
| 15 | (76) | Red Brown | White | 90.4 | 94.0 | 82.6 | −3.1 | 13.0 |
| 16 | (77) | Red Brown | White | 89.3 | 94.6 | 83.5 | −3.2 | 12.4 |
| 17 | (78) | Red Brown | White | 92.8 | 93.7 | 83.1 | −3.2 | 11.4 |
| 18 | (13) | Green Black | White | 94.2 | 93.8 | 84.2 | −3.1 | 10.6 |
| 19 | (14) | Green Black | White | 95.1 | 94.2 | 84.3 | −2.6 | 11.3 |
| 20 | (59) | Purple Black | White | 93.1 | 92.4 | 86.2 | −2.1 | 10.4 |
| Comparative Example 1 | 3-(p-dimethylaminophenyl)-3-{1,1-bis(p-dimethylaminophenyl)-ethylene-2-yl}phthalide | Green | Pale green | 90.5 | 87.0 | 75.2 | −1.3 | 19.8 |
| Comparative Example 2 | -3-(p-dimethylaminophenyl)-3-{1-p-dimethyolaminophenyl)-1-phenylethylene-2-yl}phthalide-; | Light sepia | White | 90.6 | 88.0 | 80.1 | −3.1 | 19.6 |
| Comparative Example 3 | -3-N-methyl-N-cyclohexylamino-6-methyl-7-anilinofluoran-. | Black | White | 20% or less | 20% or less | 86.3 | −1.0 | 0.2 |

As can be seen from the results shown in Table 2, the recording material according to the present invention can yield images which are capable of sufficiently absorbing near infrared rays, in particular, in the range of a wavelength of 700 to 900 nm. Therefore the images formed on the recording material according to the present invention can be read by a general optical character reader (OCR) and an image reader employing a light emitting diode or a semiconductor laser as a light source.

The background of the above-mentioned recording material is considerably light-resistant, so that it scarcely turns yellow when exposed to light.

Furthermore, the recording material according to the present invention has the advantages in that it can produce images in a nearly black color.

What is claimed is:

1. A recording material comprising at least one leuco dye having formula (I), which is colored when brought into contact with a color developer capable of inducing color formation in the leuco dye:

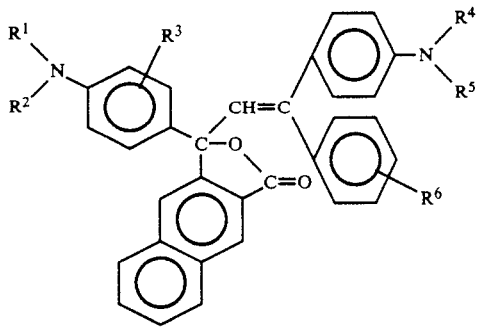

wherein $R^1$ and $R^2$ each represent an alkyl group having 1 to 6 carbon atoms, a cycloalkyl group, an aralkyl group which may have a substituent, or an aryl group which may have a substituent, which $R^1$ and $R^2$ in combination may form a ring or a morpholine ring through an oxygen atom; $R^3$ represents hydrogen, an alkyl group having 1 to 4 carbon atoms, an alkoxyl group having 1 to 4 carbon atoms or an aralkyloxy group; $R^4$ and $R^5$ each represent an alkyl group having 1 to 4 carbon atoms; and $R^6$ represents hydrogen, an alkyl group having 1 to 4 carbon atoms or a halogen.

2. The recording material as claimed in claim 1, wherein said aralkyl group represented by $R^1$ or $R^2$ is a benzyl group.

3. The recording material as claimed in claim 1, wherein said aralkyl group represented by $R^1$ or $R^2$ is a phenethyl group.

4. The recording material as claimed in claim 1, wherein said substituent of said aralkyl group represented by $R^1$ or $R^2$ is an alkyl group having 1 to 4 carbon atoms.

5. The recording material as claimed in claim 1, wherein said aryl group represented by $R^1$ or $R^2$ is a phenyl group.

6. The recording material as claimed in claim 1, wherein said substituent of said aryl group represented by $R^1$ or $R^2$ is an alkyl group having 1 to 4 carbon atoms.

7. The recording material as claimed in claim 1, wherein said substituent of said aryl group represented by $R^1$ or $R^2$ is a dialkylamino group.

8. A thermosensitive recording material comprising a substrate and a thermosensitive coloring layer formed thereon comprising at least one leuco dye having formula (I), which is colored when brought into contact with a color developer capable of inducing color formation in the leuco dye:

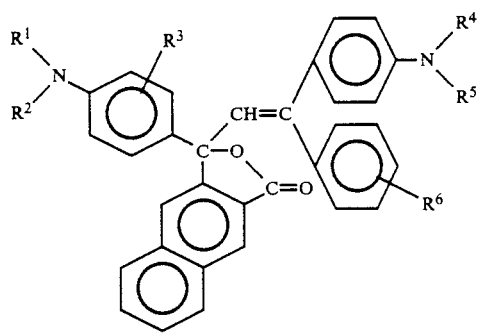

wherein $R^1$ and $R^2$ each represent an alkyl group having 1 to 6 carbon atoms, a cycloalkyl group, an aralkyl group which may have a substituent, or an aryl group which may have a substituent, which $R^1$ and $R^2$ may form a ring in combination or a morpholine ring through an oxygen atom; $R^3$ represents hydrogen, an alkyl group having 1 to 4 carbon atoms, an alkoxyl group having 1 to 4 carbon atoms, or an aralkyloxy group; $R^4$ and $R^5$ each represent an alkyl group having 1 to 4 carbon atoms; and $R^6$ represents hydrogen, an alkyl group having 1 to 4 carbon atoms, or a halogen.

9. The recording material as claimed in claim 8, wherein said aralkyl group represented by $R^1$ or $R^2$ is a benzyl group.

10. The recording material as claimed in claim 8, wherein said aralkyl group represented by $R^1$ or $R^2$ is a phenethyl group.

11. The recording material as claimed in claim 8, wherein said substituent of said aralkyl group represented by $R^1$ or $R^2$ is an alkyl group having 1 to 4 carbon atoms.

12. The recording material as claimed in claim 8, wherein said aryl group represented by $R^1$ or $R^2$ is a phenyl group.

13. The recording material as claimed in claim 8, wherein said substituent of said aryl group represented by $R^1$ or $R^2$ is an alkyl group having 1 to 4 carbon atoms.

14. The recording material as claimed in claim 8, wherein said substituent of said aryl group represented by $R^1$ or $R^2$ is a dialkylamino group.

15. A pressure-sensitive recording material comprising a coloring sheet comprising a substrate and a coloring layer formed thereon comprising at least one leuco dye having formula (I), which is colored when brought into contact with a color developer capable of inducing color formation in the leuco dye:

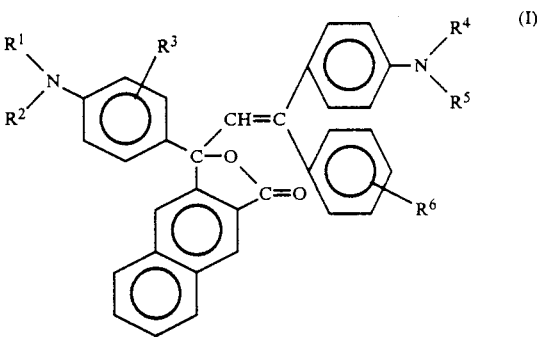

wherein $R^1$ and $R^2$ each represent an alkyl group having 1 to 6 carbon atoms, a cycloalkyl group, an aralkyl group which may have a substituent, or an aryl group which may have a substituent, which $R^1$ and $R^2$ may form a ring in combination or a morpholine ring through an oxygen atom; $R^3$ represents hydrogen, an alkyl group having 1 to 4 carbon atoms, an alkoxyl group having 1 to 4 carbon atoms, or an aralkyloxy group; $R^4$ and $R^5$ each represent an alkyl group having 1 to 4 carbon atoms; and $R^6$ represents hydrogen, an alkyl group having 1 to 4 carbon atoms, or a halogen.

16. The recording material as claimed in claim 15, wherein said aralkyl group represented by $R^1$ or $R^2$ is a benzyl group.

17. The recording material as claimed in claim 15, wherein said aralkyl group represented by $R^1$ or $R^2$ is a phenethyl group.

18. The recording material as claimed in claim 15, wherein said substituent of said aralkyl group represented by $R^1$ or $R^2$ is an alkyl group having 1 to 4 carbon atoms.

19. The recording material as claimed in claim 15, wherein said aryl group represented by $R^1$ or $R^2$ is a phenyl group.

20. The recording material as claimed in claim 15, wherein said substituent of said aryl group represented by $R^1$ or $R^2$ is an alkyl group having 1 to 4 carbon atoms.

21. The recording material as claimed in claim 15, wherein said substituent of said aryl group represented by $R^1$ or $R^2$ is a dialkylamino group.

22. The pressure-sensitive recording material as claimed in claim 15, wherein said leuco dye is microcapsuled in said coloring layer.

* * * * *

UNITED STATES PATENT AND TRADEMARK OFFICE
CERTIFICATE OF CORRECTION

PATENT NO. : 4,985,345
DATED : January 15, 1991
INVENTOR(S) : HAYAKAWA ET AL

It is certified that error appears in the above-identified patent and that said Letters Patent is hereby corrected as shown below:

Column 2, line 9, "quantities" should read -- quantity --.

Column 4, line 32, "formul" should read -- formula --;

line 42, "followings" should read --following--.

Column 13, line 9, "5'nitrophenyl)phthalide," should read -- 5'-nitrophenyl)phthalide,--;

line 62, "1,1,3-tris(2-methyl-4-hydroxy-5cylclohexylphenyl)bu-" should read -- 1,1,3-tris(2-methyl-4-hydroxy-5-cyclohexylphenyl)bu- --.

Column 16, line 5, "Alternatively," should read -- Alternatively, a --.

UNITED STATES PATENT AND TRADEMARK OFFICE
CERTIFICATE OF CORRECTION

PATENT NO. : 4,985,345
DATED : January 15, 1991
INVENTOR(S) : HAYAKAWA ET AL

It is certified that error appears in the above-identified patent and that said Letters Patent is hereby corrected as shown below:

In the table given on Columns 17 and 18, in the entry for Comparative Example 2, "-3-(p-dimethylaminophenyl)-3-{1-p-dimethyolaminophenyl)-1-phenylethylene-2-yl}phthalide-" should read -- 3-(p-dimethylaminophenyl)-3-{1-(p-dimethylaminophenyl)-1-phenylethylene-2-yl}phthalide --.

Column 18, line 62, "advantages" should read -- advantage --.

Signed and Sealed this

Third Day of November, 1992

Attest:

DOUGLAS B. COMER

Attesting Officer     Acting Commissioner of Patents and Trademarks